United States Patent
Thompson et al.

(10) Patent No.: US 10,750,605 B2
(45) Date of Patent: *Aug. 18, 2020

(54) VARIABLE FREQUENCY EXCITATION PLASMA DEVICE FOR THERMAL AND NON-THERMAL TISSUE EFFECTS

(71) Applicant: COVIDIEN LP, Mansfield, MA (US)

(72) Inventors: James E. Thompson, Frederick, CO (US); Daniel A. Friedrichs, Aurora, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/295,304

(22) Filed: Mar. 7, 2019

(65) Prior Publication Data
US 2019/0208614 A1    Jul. 4, 2019

Related U.S. Application Data

(63) Continuation of application No. 14/549,022, filed on Nov. 20, 2014, now Pat. No. 10,237,962.
(Continued)

(51) Int. Cl.
*H05H 1/46* (2006.01)
*A61B 18/04* (2006.01)
(Continued)

(52) U.S. Cl.
CPC ............. *H05H 1/46* (2013.01); *A61B 18/042* (2013.01); *A61B 18/1206* (2013.01);
(Continued)

(58) Field of Classification Search
CPC ........... A61B 2018/00583; H05H 1/46; H05H 2001/4682; H05H 2001/466
See application file for complete search history.

(56) References Cited

U.S. PATENT DOCUMENTS

| 3,434,476 A | 3/1969 | Shaw et al. |
| 3,492,074 A | 1/1970 | Rendina |

(Continued)

FOREIGN PATENT DOCUMENTS

| CN | 2391565 Y | 8/2000 |
| DE | 3710489 A1 | 11/1987 |

(Continued)

OTHER PUBLICATIONS

Ward et al., "A Significant New Contribution to Radical Head and Neck Surgery"; Arch Otolaryngology, Head and Neck Surg., vol. 115 pp. 921-923 (Aug. 1989).
(Continued)

*Primary Examiner* — Ronald Hupczey, Jr.
(74) *Attorney, Agent, or Firm* — Carter, DeLuca & Farrell LLP

(57) ABSTRACT

A plasma system is disclosed. The plasma system includes a plasma instrument having an elongated body defining a lumen therethrough and a first electrode and a second electrode; an ionizable media source in fluid communication with the lumen and configured to supply ionizable media thereto; and a variable frequency energy source adapted to be coupled to the first and second electrodes and configured to supply energy to the first and second electrodes sufficient to ignite ionizable media supplied by the ionizable media source to generate a plasma influent, wherein a frequency of the energy is adjustable to modify at least one property of the plasma effluent.

17 Claims, 6 Drawing Sheets

Related U.S. Application Data

(60) Provisional application No. 61/945,000, filed on Feb. 26, 2014.

(51) Int. Cl.
*A61B 18/12* (2006.01)
*A61B 18/00* (2006.01)

(52) U.S. Cl.
CPC ............... *A61B 2018/00732* (2013.01); *A61B 2018/00863* (2013.01); *H05H 2001/466* (2013.01); *H05H 2245/122* (2013.01); *H05H 2277/10* (2013.01)

(56) References Cited

U.S. PATENT DOCUMENTS

| | | | |
|---|---|---|---|
| 3,687,832 A | 8/1972 | Fydelor et al. |
| 3,903,891 A | 9/1975 | Brayshaw |
| 4,035,720 A | 7/1977 | Harvey |
| 4,188,426 A | 2/1980 | Auerbach |
| 4,517,495 A | 5/1985 | Piepmeier |
| 4,699,082 A | 10/1987 | Hakim |
| 4,837,484 A | 6/1989 | Eliasson et al. |
| 4,855,563 A | 8/1989 | Beresnev et al. |
| 5,013,959 A | 5/1991 | Kogelschatz |
| 5,041,110 A | 8/1991 | Fleenor |
| 5,194,740 A | 3/1993 | Kogelschatz et al. |
| 5,466,424 A | 11/1995 | Kusano et al. |
| 5,669,904 A | 9/1997 | Platt, Jr. et al. |
| 5,688,357 A | 11/1997 | Hanawa |
| 5,776,255 A | 7/1998 | Asaba et al. |
| 5,780,862 A | 7/1998 | Siess |
| 5,866,871 A | 2/1999 | Birx |
| 5,869,832 A | 2/1999 | Wang et al. |
| 5,892,198 A | 4/1999 | Barnes et al. |
| 5,945,790 A | 8/1999 | Schaefer |
| 6,027,601 A | 2/2000 | Hanawa |
| 6,153,852 A | 11/2000 | Blutke et al. |
| 6,159,208 A | 12/2000 | Hovda et al. |
| 6,172,324 B1 | 1/2001 | Birx |
| 6,203,542 B1 | 3/2001 | Ellsberry et al. |
| 6,264,650 B1 | 7/2001 | Hovda et al. |
| 6,326,584 B1 | 12/2001 | Jewett et al. |
| 6,345,588 B1 | 2/2002 | Stimson |
| 6,376,972 B1 | 4/2002 | Tarasenko et al. |
| 6,392,210 B1 | 5/2002 | Jewett et al. |
| 6,407,513 B1 | 6/2002 | Vollkommer et al. |
| 6,432,103 B1 | 8/2002 | Ellsberry et al. |
| 6,464,695 B2 | 10/2002 | Hovda et al. |
| 6,468,270 B1 | 10/2002 | Hovda et al. |
| 6,488,825 B1 | 12/2002 | Hilliard |
| 6,501,079 B1 | 12/2002 | Furuya |
| 6,544,261 B2 | 4/2003 | Ellsberry et al. |
| 6,602,248 B1 | 8/2003 | Sharps et al. |
| 6,631,693 B2 | 10/2003 | Hilliker |
| 6,657,173 B2 | 12/2003 | Flugstad et al. |
| 6,772,012 B2 | 8/2004 | Ricart et al. |
| 6,837,884 B2 | 1/2005 | Woloszko |
| 6,876,155 B2 | 4/2005 | Howald et al. |
| 6,887,339 B1 | 5/2005 | Goodman et al. |
| 7,004,941 B2 | 2/2006 | Tvinnereim et al. |
| 7,070,596 B1 | 7/2006 | Woloszko et al. |
| 7,090,672 B2 | 8/2006 | Underwood et al. |
| 7,094,215 B2 | 8/2006 | Davison et al. |
| 7,156,842 B2 | 1/2007 | Sartor et al. |
| 7,169,256 B2 | 1/2007 | Dhindsa et al. |
| 7,179,255 B2 | 2/2007 | Lettice et al. |
| 7,270,659 B2 | 9/2007 | Ricart et al. |
| 7,318,823 B2 | 1/2008 | Sharps et al. |
| 7,331,956 B2 | 2/2008 | Hovda et al. |
| RE40,156 E | 3/2008 | Sharps et al. |
| 7,387,625 B2 | 6/2008 | Hovda et al. |
| 7,393,351 B2 | 7/2008 | Woloszko et al. |
| 7,408,329 B2 | 8/2008 | Wiedemuth |
| 7,491,200 B2 | 2/2009 | Underwood |
| 7,708,733 B2 | 5/2010 | Sanders et al. |
| 7,879,033 B2 | 2/2011 | Sartor et al. |
| 8,157,795 B2 | 4/2012 | Sartor et al. |
| 10,237,962 B2* | 3/2019 | Thompson ........... A61B 18/042 |
| 2003/0038912 A1 | 2/2003 | Broer et al. |
| 2003/0069576 A1 | 4/2003 | Tanrisever |
| 2003/0088245 A1 | 5/2003 | Woloszko et al. |
| 2003/0158545 A1 | 8/2003 | Hovda et al. |
| 2005/0004634 A1 | 1/2005 | Ricart et al. |
| 2005/0010205 A1 | 1/2005 | Hovda et al. |
| 2005/0113824 A1 | 5/2005 | Sartor et al. |
| 2005/0119650 A1 | 6/2005 | Sanders et al. |
| 2005/0149012 A1 | 7/2005 | Penny et al. |
| 2005/0153159 A1 | 7/2005 | Sugiyama et al. |
| 2005/0234439 A1 | 10/2005 | Underwood |
| 2005/0261754 A1 | 11/2005 | Woloszko |
| 2006/0091109 A1 | 5/2006 | Partlo et al. |
| 2006/0200122 A1 | 9/2006 | Sartor et al. |
| 2007/0010809 A1 | 1/2007 | Hovda et al. |
| 2007/0027440 A1 | 2/2007 | Altshuler et al. |
| 2007/0029500 A1 | 2/2007 | Coulombe et al. |
| 2007/0045561 A1 | 3/2007 | Cooper |
| 2007/0106288 A1 | 5/2007 | Woloszko et al. |
| 2008/0122368 A1 | 5/2008 | Saito et al. |
| 2008/0125772 A1 | 5/2008 | Stone et al. |
| 2010/0125267 A1 | 5/2010 | Lee et al. |
| 2010/0204690 A1 | 8/2010 | Bigley et al. |
| 2012/0215216 A1 | 8/2012 | Friedrichs et al. |
| 2014/0224643 A1 | 8/2014 | Collins et al. |
| 2014/0225495 A1 | 8/2014 | Koo et al. |
| 2014/0225498 A1 | 8/2014 | Koo et al. |
| 2014/0228833 A1 | 8/2014 | Friedrichs et al. |
| 2014/0257276 A1 | 9/2014 | Sartor |

FOREIGN PATENT DOCUMENTS

| | | |
|---|---|---|
| DE | 4139029 A1 | 6/1993 |
| DE | 4326037 A1 | 2/1995 |
| DE | 9117019 U1 | 3/1995 |
| DE | 19524645 A1 | 2/1997 |
| DE | 19537897 A1 | 3/1997 |
| DE | 9117299 U1 | 3/2000 |
| DE | 19848784 A1 | 5/2000 |
| DE | 29724247 U1 | 8/2000 |
| EP | 0956827 A1 | 11/1999 |
| EP | 2469699 A2 | 6/2012 |
| EP | 2591743 A1 | 5/2013 |
| EP | 2765838 A2 | 8/2014 |
| FR | 1340509 A | 10/1963 |
| JP | 61159953 A | 7/1986 |
| JP | 62130777 | 6/1987 |
| JP | 2000286094 A | 10/2000 |
| JP | 2005276618 A | 10/2005 |
| JP | 2006310101 A | 11/2006 |
| JP | 2008041495 A | 2/2008 |
| JP | 2010242857 A | 10/2010 |
| KR | 100734954 B1 | 7/2007 |
| SU | 1438745 A1 | 11/1988 |
| WO | 2009080273 A1 | 7/2009 |
| WO | 2009146439 A1 | 12/2009 |
| WO | 2011/055368 A2 | 5/2011 |

OTHER PUBLICATIONS

Lieberman et al., "Capacitive Discharges", Principles of Plasma Discharges and Materials Processing, John Wiley & Son, Inc. (2005) pp. 387-460.

Moore et al., "Confined Geometry Interactions of Downstream RF-Excited Atmospheric Plasma Wires", IEEE Transactions on Plasma Science, 0093-3813, (2008) pp. 1-2.

Walsh et al., "Contrasting Characteristics of Pulsed and Sinusoidal Cold Atmospheric Plasma Jets", Applied Physics Letters, 88, 171501 (2006) pp. 1-3.

Cho et al., "Coplanar ac Discharges Between Cylindrical Electrodes With a Nanoporous Alumina Dielectric: Modular Dielectric Barrier Plasma Devices", IEEE Transactions on Plasma Science, vol. 33, No. 2, (Apr. 2005) pp. 378-379.

(56) References Cited

OTHER PUBLICATIONS

Xu et al., "DBD Plasma Jet in Atmospheric Pressure Argon", IEEE Transactions on Plasma Science, vol. 36, No. 4, (Aug. 2008), pp. 1352-1353.
Alfred Grill, "Electron Cyclotron Resonance Plasmas", Cold Plasma in Materials Fabrication, IEEE Press (1994) pp. 40-43.
Brand et al., "Electrosurgical Debulking of Ovarian Cancer: A New Technique Using the Argon Beam Coagulator"; Gynecologic Oncology 39 pp. 115-118 (1990).
Grund et al., "Endoscopic Argon Plasma . . . Flexible Endoscopy"; Endoscopic Surgery and Allied Technologies, No. 1, vol. 2, pp. 42-46 (Feb. 1994).
Waye et al., "Endoscopic Treatment Options"; Techniques in Therapeutic Endoscopy, pp. 1.7-1.15, (1987).
B.D. Cullity, "Introduction to Magnetic Materials", University of Notre Dame; Addison-Wesley Publishing Company, Reading MA., (1972) pp. 23-28.
Brian Chapman, "Matching Networks", Glow Discharge Processes, John Wiley & Sons Inc., NY, (1980) pp. 153-172.
Yin et al., "Miniaturization of Inductively Coupled Plasma Sources", IEEE Transactions on Plasma Science, vol. 27, No. 5, (Oct. 1999) pp. 1516-1524.
Park et al., "Nanoporous Anodic Alumina Film on Glass: Improving Transparency by an Ion-Drift Process", Electrochemical and Solid-State Letters, 8 (3) (2005), pp. D5-D7.
P.A. Tulle, "Off-Resonance Microwave-Created Plasmas", Plasma Physics, Pergamon Press (1973) vol. 15, pp. 971-976.
Lieberman et al., "Ohmic Heating", Principles of Plasma Discharges and Materials Processing, John Wiley & Son, Inc. (2005) pp. 97-98.
Lieberman et al., "Optical Actinometry", Principles of Plasma Discharges and Materials Processing, John Wiley & Son, Inc. (2005) pp. 277-279.
Cho et al., "Ozone Production by Nanoporous Dielectric Barrier Glow Discharge in Atmospheric Pressure Air", Applied Physics Letters, 92, 101504, (2008) pp. 1-3.
Lieberman et al., "Particle and Energy Balance in Discharges", Principles of Plasma Discharges and Materials Processing, John Wiley & Son, Inc. (2005) pp. 329-381.
Woloszko et al., "Plasma Characteristics of Repetitively-Pulsed Electrical Discharges in Saline Solutions Used for Surgical Procedures", IEEE Transactions of Plasma Science, vol. 30, No. 3, (Jun. 2002) pp. 1376-1383.
Stoffels et al., "Plasma Needle for In Vivo Medical Treatment: Recent Developments and Perspectives", Plasma Sources Science and Technology 15 (2006) pp. 169-180.
Schaper et al., "Plasma Production and Vapour Layer Production at a Pulse Power Electrode in Saline Solution:", (2008) www.escampig2008.csic.es/PosterSessions/100.
Akitsu et al., "Plasma Sterilization Using Glow Discharge at Atmospheric Pressure", Surface & Coatings Technology 193, (2005) pp. 29-34.
Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.
Brian Chapman, "Secondary Electron Emission", Glow Discharge Processes, John Wiley & Sons Inc., NY, (1980) pp. 82-138.
Moore et al., "Sensitive, Nonintrusive, In-Situ Measurement of Temporally and Spatially Resolved Plasma Electric Fields", Physical Review Letters, vol. 52, No. 7, (Feb. 13, 1984) pp. 538-541.
Lieberman et al., "Sheaths", Principles of Plasma Discharges and Materials Processing, John Wiley & Son, Inc. (2005) pp. 11-14.
Farin et al., Technology of Argon Plasma . . . Endoscopic Applications; Endoscopic Surgery and Allied Technologies, No. 1, vol. 2, pp. 71-77 (Feb. 1994).

Lieberman et al., "The Collisionless Sheath", Principles of Plasma Discharges and Materials Processing, John Wiley & Son, Inc. (2005) pp. 167-206.
Gupta et al., "The Potential of Pulsed Underwater Streamer Discharges as a Disinfection Technique", IEEE Transactions on Plasma Science, vol. 36, No. 4, (Aug. 2008) pp. 1621-1632.
Mark H. Mellow, "The Role of Endoscopic Laser Therapy in Gastrointestinal Neoplasms"; Advanced Therapeutic Endoscopy, pp. 17-21, (1990).
Silverstein et al., "Thermal Coagulation Therapy for Upper Gastrointestinal Bleeding"; Advanced Therapeutic Endoscopy, pp. 79-84, 1990.
Sobolewski, Mark A., "Current and Voltage Measurements in the Gaseous Electronics Conference RF Reference Cell". J. Res. Natl. Inst. Stand. Technol. 100, 341; Apr. 1995.
Hernandez et al., "A Controlled Study of the Argon Beam Coagultor for Partial Nephrectomy"; The Journal of Urology, vol. 143, May 1990 J. Urol. 143: pp. 1062-1065.
Partial European Search Report from Application No. EP 14158043.1 dated Jun. 10, 2014.
Sosnin et al., "Applications of Capacitive and Barrier Discharge Excilamps in Photoscience", Journal of Photochemistry and Photobiiology, vol. 7, pp. 145-163 (2006).
Lomaev et al., Capatitive and Barrier Discharge Excilamps and Their Applications (Review); Instruments and Experimental Techniques, 2006; vol. 49, No. 5; pp. 595-616.
Lomaev et al., "Excilamps and their Applications", Progress in Quantum Electronics 36; pp. 51-97; (2012).
Oppenlander et al., "Mercury-free Vacuum—(VUV) and UV Excilamps: Lamps of the Future?" Dept. of Process Engineering; IUVA News, vol. 7, No. 4; pp. 16-20, (Dec. 2005).
Tarasenko et al., "VUV and UV Excilamps and Their Applications", Proc. of SPIE, vol. 6261 pp. 626136-1 through626136-10; (2006).
U.S. Appl. No. 08/619,380; dated Mar. 21, 1996; inventor: Gene H. Arts.
U.S. Appl. No. 08/621,151; dated Mar. 21, 1996; inventor: Robert B. Stoddard.
U.S. Appl. No. 08/878,694; dated Jun. 19, 1997; inventor: Lawrence K. Pacer.
U.S. Appl. No. 09/270,856; dated Mar. 17, 1999; inventor: Gene H. Arts.
U.S. Appl. No. 09/504,640; dated Feb. 16, 2000; inventor: James Steven Cunningham.
U.S. Appl. No. 09/666,312; dated Sep. 21, 2000; inventor: Robert C. Platt.
U.S. Appl. No. 08/383,162; dated Feb. 3, 1995; inventor: Lawrence K. Pacer; copy attached.
EP Search Report for EP 14 20 0621 dated Jul. 6, 2015.
Japanese Official Action for JP 2014-260295 dated Sep. 8, 2015.
Notice of Final Rejection and English Language Translation issued in Japanese Appl. No. JP 2014-260295 dated Mar. 3, 2016.
Chinese Office Action issued in Appl. No. CN 201410838378.9 dated Dec. 1, 2016.
Chinese Office Action, and English language translation, issued in Appl. No. CN 201410838378.9 dated Aug. 2, 2017.
Japanese Office Action, and English language translation, issued in Appl. No. JP 2014-260295, dated Sep. 7, 2017 (8 pages).
Laroussi et al., "Plasma Medicine: Applications of Low-Temperature Gas Plasmas in Medicine and Biology", 2012, Cambridge University Press, 30-31.
U.S. Appl. No. 08/383,162; dated Feb. 3, 1995; inventor: Lawrence K. Pacer.
European Examination Report dated Mar. 26, 2020 issued in corresponding EP Appln. No. 14200621.2.

\* cited by examiner

VARIABLE FREQUENCY EXCITATION PLASMA DEVICE FOR THERMAL AND NON-THERMAL TISSUE EFFECTS

CROSS-REFERENCE TO RELATED APPLICATION

The present application is a continuation of U.S. patent application Ser. No. 14/549,022, filed on Nov. 20, 2014, now U.S. Pat. No. 10,237,962, which claims the benefit of and priority to U.S. Provisional Patent Application No. 61/945,000, filed Feb. 26, 2014, the entire contents of which are incorporated by reference herein.

BACKGROUND

Technical Field

The present disclosure relates to plasma devices and processes for surface processing and tissue treatment. More particularly, the disclosure relates to a bipolar coagulation handpiece for generating chemically reactive, plasma-generated species.

Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring plasma electron temperature and electron density. In addition, adjusting spatial, temporal and temperature properties of the plasma creates specific changes to the material being irradiated by the plasma species and associated photon fluxes. Plasmas are also capable of generating photons including energetic ultraviolet photons that have sufficient energy to initiate photochemical and photocatalytic reaction paths in biological and other materials that are irradiated by the plasma photons. There is a need for plasma devices that are configured for providing various tissue effects by varying above-described properties of the plasma.

SUMMARY

Plasmas have broad applicability and provide alternative solutions to industrial, scientific and medical needs, especially workpiece (e.g., tissue) surface treatment at any temperature range. Plasmas may be delivered to the workpiece, thereby affecting multiple changes in the properties of materials upon which the plasmas impinge. Plasmas have the unique ability to create large fluxes of radiation (e.g., ultraviolet), ions, photons, electrons and other excited-state (e.g., metastable) species which are suitable for performing material property changes with high spatial, material selectivity, and temporal control. Plasmas may also remove a distinct upper layer of a workpiece with little or no effect on a separate underlayer of the workpiece or it may be used to selectively remove a particular tissue from a mixed tissue region or selectively remove a tissue with minimal effect to adjacent organs of different tissue type.

The plasma species are capable of modifying the chemical nature of tissue surfaces by breaking chemical bonds, substituting or replacing surface-terminating species (e.g., surface functionalization) through volatilization, gasification or dissolution of surface materials (e.g., etching). With proper techniques, material choices and conditions, it is possible to remove one type of tissue entirely without affecting a nearby different type of tissue. Controlling plasma conditions and parameters (including S-parameters, V, I, $\Theta$, and the like) allows for the selection of a set of specific particles, which, in turn, allows for selection of chemical pathways for material removal or modification as well as selectivity of removal of desired tissue type.

According to one embodiment of the present disclosure, a plasma system is disclosed. The plasma system includes a plasma instrument having an elongated body defining a lumen therethrough and a first electrode and a second electrode; an ionizable media source in fluid communication with the lumen and configured to supply ionizable media thereto; and a variable frequency energy source adapted to be coupled to the first and second electrodes and configured to supply energy to the first and second electrodes sufficient to ignite ionizable media supplied by the ionizable media source to generate a plasma influent, wherein a frequency of the energy is adjustable to modify at least one property of the plasma effluent.

According to one aspect of the above embodiment, at least one of the variable frequency energy source or the plasma instrument includes controls for adjusting the frequency.

According to another aspect of the above embodiment, the ionizable media source is adapted to be coupled to the variable frequency energy source.

According to a further aspect of the above embodiment, wherein the variable frequency energy source is configured to adjust the frequency based on a flow rate of the ionizable media from the ionizable media source. The plasma instrument may include an applicator tip coupled to a distal end of the elongated body. The applicator tip may also define a second lumen in fluid communication with the lumen of the elongated body. The first electrode may be disposed on an outer surface of the applicator tip. The second electrode may be disposed within at least one of the lumen of the elongated body or the second lumen.

According to one aspect of the above embodiment, the frequency is adjustable to a first frequency at which the plasma effluent is at a first temperature and a second frequency higher than the first frequency at which the plasma effluent is at a second temperature higher than the first temperature.

According to another aspect of the above embodiment, the energy source includes: a non-resonant radio frequency output stage configured to output an excitation waveform; and a controller coupled to the non-resonant radio frequency output stage, the controller configured to adjust the frequency of the excitation waveform on a cycle-by-cycle basis. The non-resonant radio frequency output stage includes: a DC-DC buck converter configured to output a DC waveform, the DC-DC buck converter including at least one first switching element operated at a first duty cycle. The non-resonant radio frequency output stage further includes: a DC-AC boost converter coupled to the DC-DC buck converter and including at least one second switching element operated at a second duty cycle, the DC-AC boost converter configured to convert the DC waveform to generate the excitation waveform. The controller is coupled to the DC-DC buck converter and the DC-AC boost converter and the controller is further configured to adjust the second duty cycle to adjust the duty cycle of the excitation waveform.

According to another embodiment of the present disclosure, a method is disclosed. The method includes: supplying ionizable media from an ionizable media source to a plasma instrument, the plasma instrument including an elongated body defining a lumen therethrough and first and second electrodes; supplying an excitation waveform from a variable frequency energy source to the first and second electrodes to ignite ionizable media supplied by the ionizable media source and to generate a plasma influent; and adjusting a frequency of the excitation waveform to modify at least one property of the plasma effluent.

According to one aspect of the above embodiment, adjustment of the frequency includes adjustment a variable setting element disposed on the plasma instrument. Adjustment of the frequency includes inputting a desired frequency using a frequency user interface of the variable frequency energy source. Adjustment of the frequency includes inputting the frequency based on a flow rate of the ionizable media from the ionizable media source. Adjustment of the frequency includes setting to at least one of a first frequency at which the plasma effluent is at a first temperature and a second frequency higher than the first frequency at which the plasma effluent is at a second temperature higher than the first temperature.

According to one aspect of the above embodiment, supplying the excitation waveform includes operating at least one switching element of a DC-AC boost converter at a duty cycle to convert a DC waveform to generate the excitation waveform. Adjustment of the frequency includes adjustment the duty cycle.

BRIEF DESCRIPTION OF THE DRAWINGS

The accompanying drawings, which are incorporated in and constitute a part of this specification, illustrate exemplary embodiments of the disclosure and, together with a general description of the disclosure given above, and the detailed description of the embodiments given below, serve to explain the principles of the disclosure, wherein.

DETAILED DESCRIPTION

Figure 1:
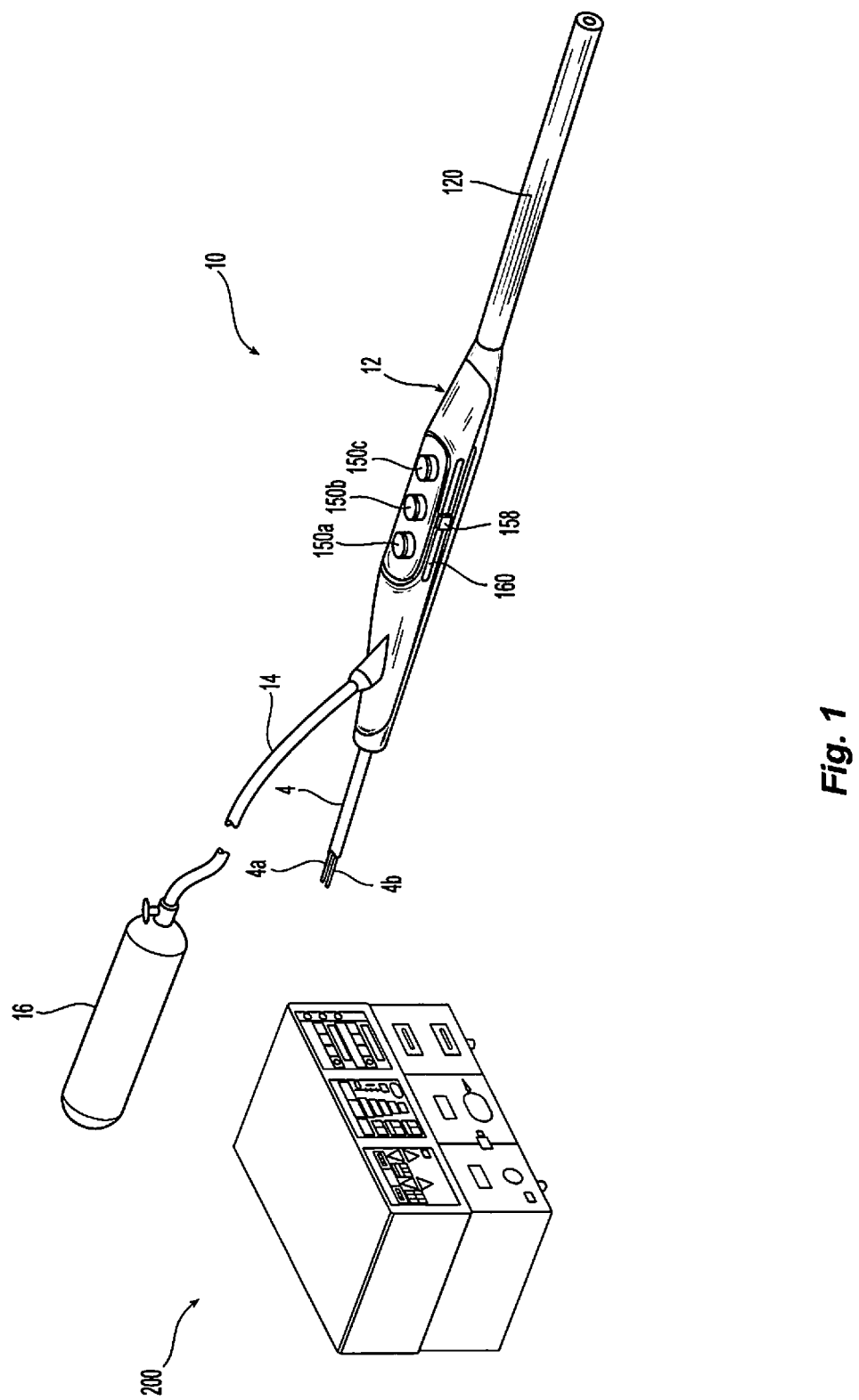
FIG. 1 is a perspective view of a plasma system according to the present disclosure.

Embodiments of the presently disclosed electrosurgical system, apparatus and/or device are described in detail with reference to the drawings, in which like reference numerals designate identical or corresponding elements in each of the several views. As used herein the term "distal" refers to that portion of the electrosurgical system, apparatus and/or device, or component thereof, that are farther from the user, while the term "proximal" refers to that portion of the electrosurgical system, apparatus and/or device, or component thereof, that are closer to the user.

In general, referring to FIG. 1, the present disclosure provides an electrosurgical plasma system 10 including a source of ionizable media 16 and an electrosurgical generator 200 configured to output energy at a variable frequency. The plasma system 10 also includes a plasma instruments 12 adapted to be coupled to the source of ionizable media 16 and to the electrosurgical generator 200. The plasma instrument 12 and/or the generator 200 include controls for adjusting the frequency of the electrosurgical generator 200, which in turn, adjusts one or more properties (e.g., temperature) of a plasma effluent generated by the plasma instrument 12. This allows for tailoring of the plasma effluent to achieve desired tissue effects. In embodiments, frequency may be adjusted in response to automated input (e.g., by the generator 200 in response to detected tissue and/or energy properties, ionizable media flow, and combinations thereof) and/or user input (e.g., selecting one or more operational mode).

Plasmas according to the present disclosure may be used to coagulate, cauterize, or otherwise treat tissue through direct application of high-energy plasma. In particular, kinetic energy transfer from the plasma to the tissue causes healing, and thus, affects thermal coagulation of bleeding tissue. In embodiments, plasma beam coagulation may be accomplished using a handheld electrosurgical instrument having one or more electrodes energizable by an electrosurgical generator, which outputs a high-intensity electric field suitable for forming plasma using ionizable media (e.g., inert gas).

The plasma system 10 according to the present disclosure is capable of generating plasmas having a temperature from about 60° C. to about 300° C. ("high temperature plasmas"), in embodiments from about 20° C. to about 60° C. ("low temperature plasmas"). These temperatures for low temperature plasmas represent average temperatures since the particles are not in thermal equilibrium so some particles may have relatively high temperatures, however, these high temperature particles are a small portion of the plasma, so the average plasma temperature is low.

The high-temperature plasmas cause thermal effects upon tissue by delivering a stream of high-temperature ionized argon gas through an electric arc. Effects of these instruments are purely thermal and are similar to tissue effects obtained using a handheld butane torch, which also emits plasma, in the form of fire. These types of plasmas are well-suited for coagulating, cutting, vaporizing or otherwise treating tissue.

The low-temperature plasmas may be generated using corona discharges and affect tissue through non-thermal mechanisms. Plasmas produced through corona discharge ionize a small portion of the ionizable media (e.g., feedstock gas), causing the plasma to have a low average temperature. These low-temperature plasma discharges affect tissue through electroporation and production of reactive species. These types of plasmas are also well-suited for wound sterilization, drug delivery, wound closure, and other medical and surgical procedures. In embodiments, low-temperature plasma may be used for application of various bioactive agents Plasmas according to the present disclosure may be produced by DC or AC pulses. Low-temperature plasmas may be produced by applying low DC or AC pulses to the electrodes of the instrument at low duty cycles. While high-temperature plasmas may be produced by applying high frequency DC or AC pulses at high duty cycles. In embodiments, the impedance of the instrument (e.g., electrodes and other electrically-coupling components) may be entirely capacitive, thus, increasing frequencies encounter lower impedance in the instrument, allowing more power to be applied to the ionization process. A greater degree of ionization also increases the plasma temperature. Varying the gas flow rate, pulse width, and repetition rate may also be used to adjust the amount of ionization.

The plasma system 10 according to the present disclosure provides for generation of both non-thermal and thermal plasmas. The generator 200 of the presently disclosed plasma system 10 allows for adjustment of the frequency of the plasma excitation waveform. The generator 200 combines these features into a single apparatus, which improves utility of both technologies (e.g., thermal and non-thermal plasmas) and allows for seamless transition between both applications.

Plasmas according to the present disclosure may be generated using electrical energy that is delivered as either direct current (DC) electricity or alternating current (AC) electricity at frequencies from about 0.1 hertz (Hz) to about 100 gigahertz (GHz), including radio frequency ("RF", from about 0.1 MHz to about 100 MHz) and microwave ("MW", from about 0.1 GHz to about 100 GHz) bands, using appropriate generators, electrodes, and/or antennas. In embodiments, various properties of the plasma according to the present disclosure may be modified by adjusting excitation frequency, operating voltage, current, levels, phase, electron temperature and density, and combinations thereof.

With continued reference to FIG. 1, a plasma system 10 will now be described in detail. The system 10 includes a plasma instrument 12 that is coupled to a generator 200, an ionizable media source 16 which may also include an optional precursor source (not shown). The generator 200 includes any suitable components for delivering power to the plasma instrument 12. The generator 200 may be any radio frequency generator or other suitable power source capable of producing power to ignite the ionizable media to generate plasma. In embodiments, electrosurgical energy is supplied to the instrument 12 by the generator 200 through an instrument cable 4. The cable 4 includes a supply lead 4a connecting the plasma instrument 12 to an active terminal 230 (FIG. 3) of the generator 200 and a return lead connecting the instrument 12 to a return terminal 232 (FIG. 3) of the generator 200. The plasma instrument 12 may be utilized as an electrosurgical pencil for application of plasma to tissue. The generator 200 may be an electrosurgical generator that is adapted to supply the instrument 12 with electrical power at a frequency from about 100 kHz to about 4 MHz, in embodiments the frequency may be from about 200 kHz to about 3 MHz, in further embodiments the frequency may be from about 300 kHz to about 1 MHz.

Figure 2:
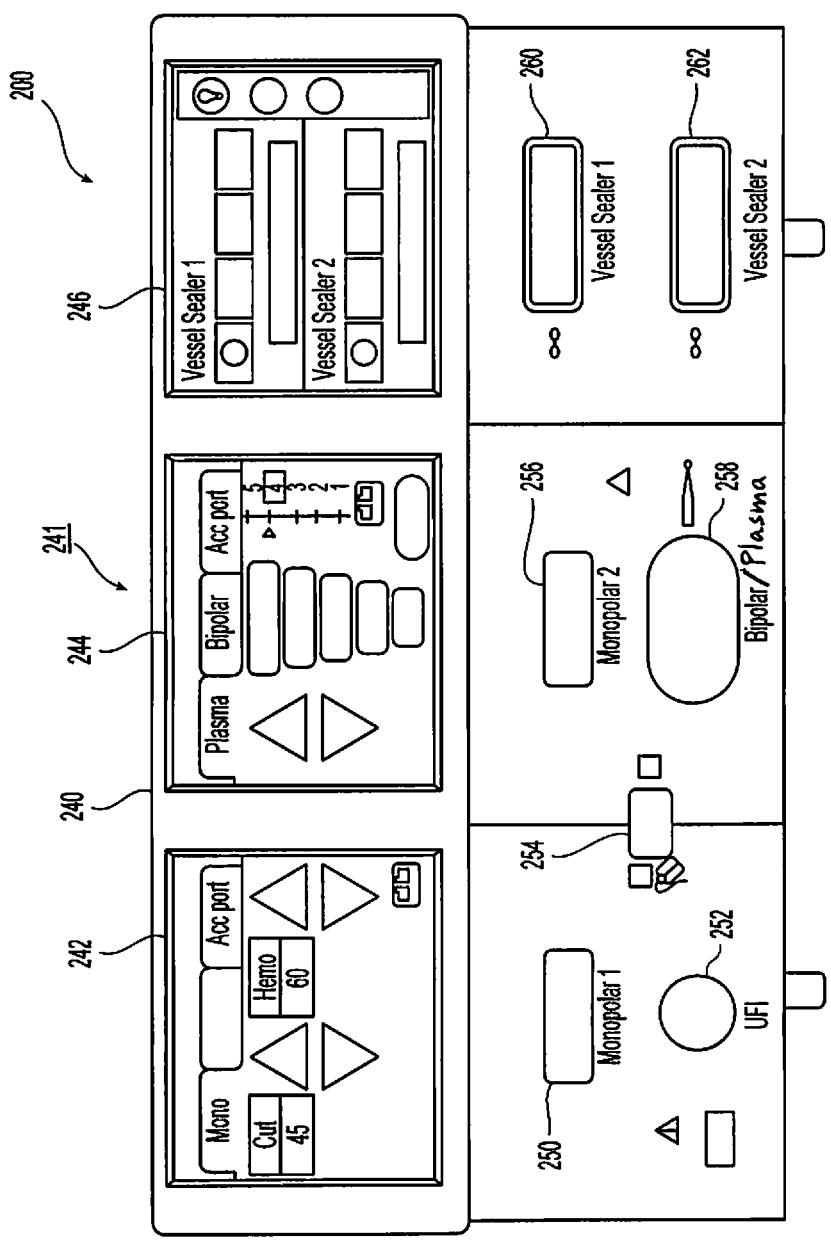
FIG. 2 is a front elevational view of one embodiment of an electrosurgical generator according to the present disclosure.
Figure 5:
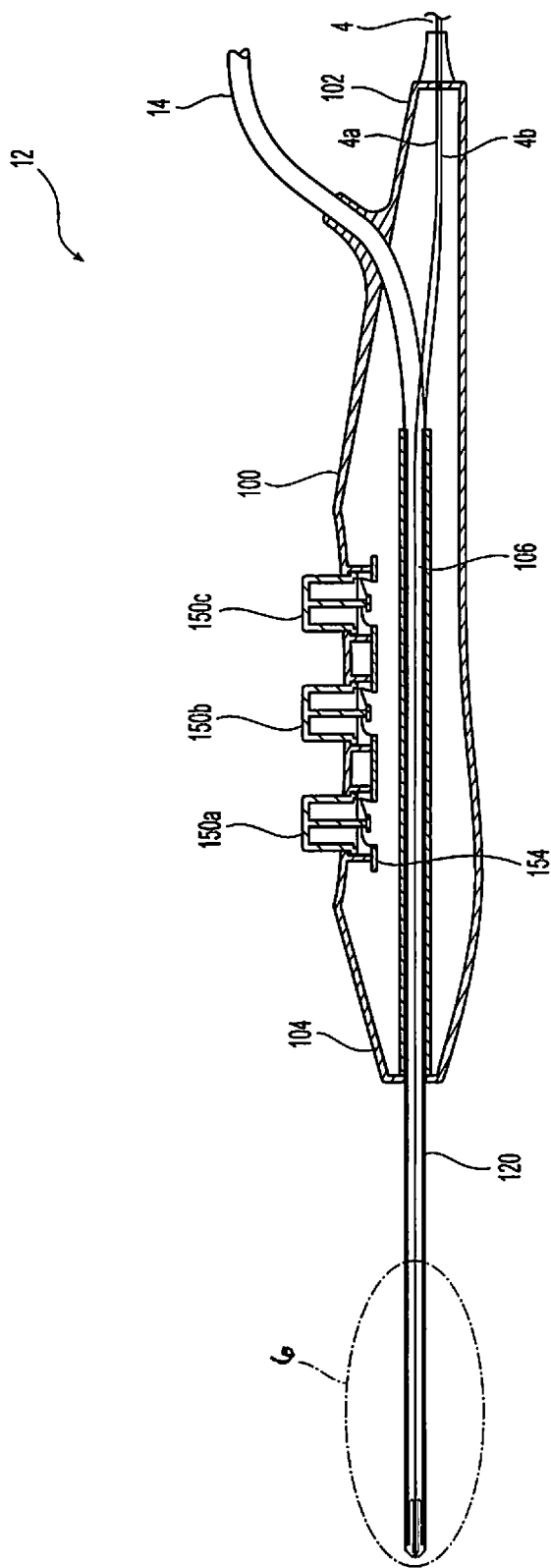
FIG. 5 is a longitudinal cross-sectional, side view of the plasma instrument of the embodiment of FIG. 1 according to the present disclosure.
Figure 6:
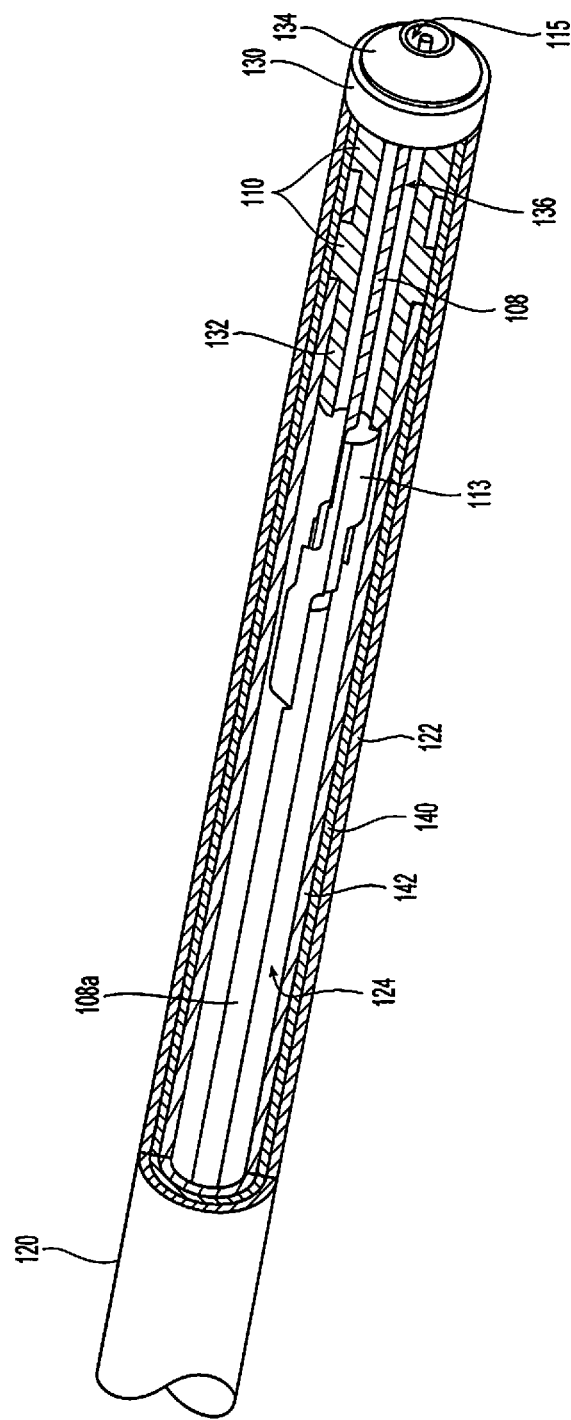
FIG. 6 is a partial cross-sectional, perspective view of the enlarged area 6 as indicated in FIG. 5 of an elongated body of the plasma instrument embodiment of FIG. 1 according to the present disclosure.

With reference to FIG. 2, a front face 240 of the generator 200 is shown. The generator 200 may be of any suitable type (e.g., electrosurgical, microwave, etc.) and may include a plurality of connectors 250-262 to accommodate various types of electrosurgical instruments (e.g., electrosurgical forceps, electrosurgical pencils, ablation probes, etc.) in addition to the plasma instrument 12 as shown in FIGS. 1, 5, and 6.

The generator 200 includes a user interface 241 having one or more display screens 242, 244, 246 for providing the user with variety of output information (e.g., frequency setting, intensity settings, treatment complete indicators, etc.). Each of the screens 242, 244, 246 is associated with corresponding connector 250, 252, 254, 256, 258, 260, and 262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., plasma instrument 12, etc.). The user then adjusts inputs by simply touching corresponding menu options.

Screen 242 controls monopolar output and the devices connected to the connectors 250 and 252. Connector 250 is configured to couple to a monopolar electrosurgical instrument (e.g., electrosurgical pencil) and connector 252 is configured to couple to a foot switch (not shown). The foot switch provides for additional inputs (e.g., replicating inputs of the generator 200). Screen 244 controls monopolar, plasma and bipolar output and the devices connected to the connectors 256 and 258. Connector 256 is configured to couple to other monopolar instruments. Connector 258 is configured to couple to plasma instrument 12. Connector 254 may be used to connect to one or more return electrode pads (not shown). Screen 246 controls plasma procedures performed by the plasma instrument 12 that may be plugged into the connectors 260 and 262.

Figure 3:
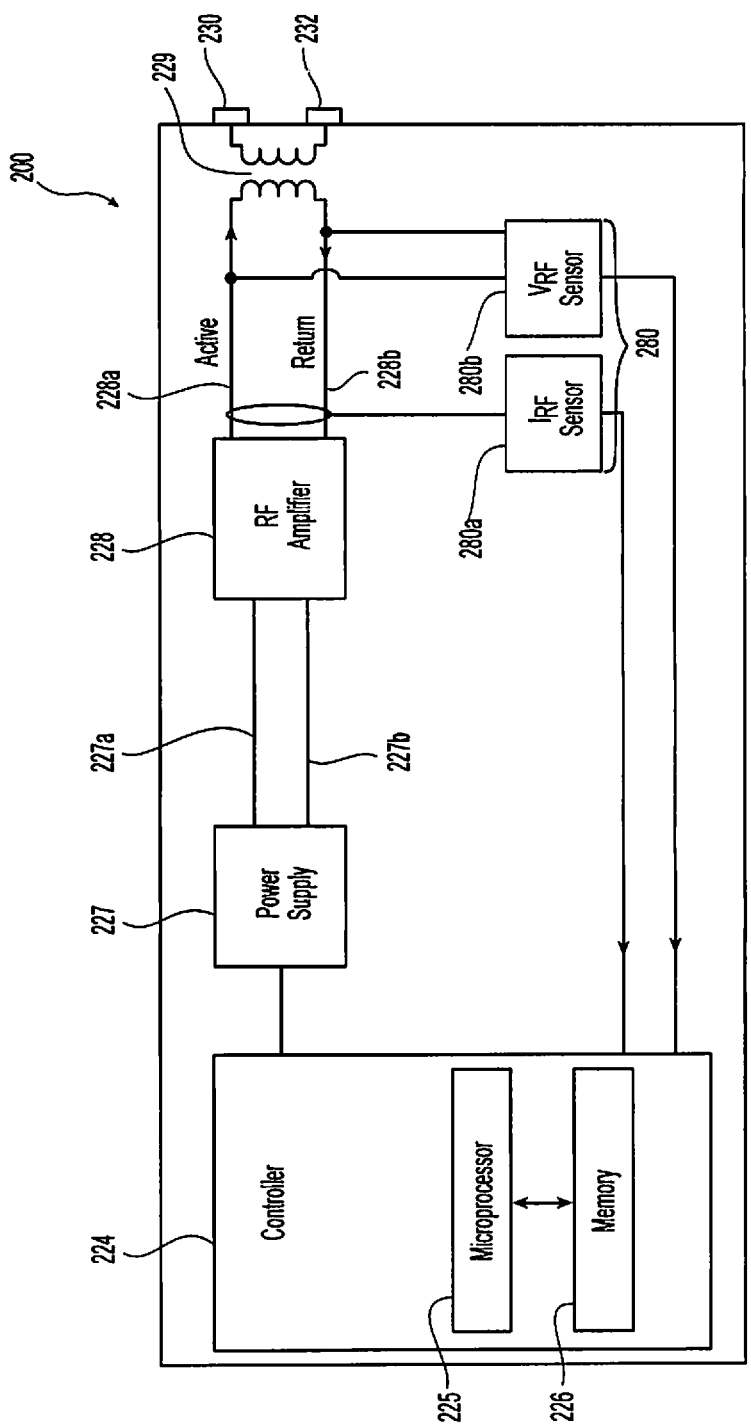
FIG. 3 is a schematic, block diagram of the embodiment of the electrosurgical generator of FIG. 2 according to the present disclosure.

FIG. 3 shows a schematic block diagram of the generator 200 configured to output electrosurgical energy. The generator 200 includes a controller 224, a power supply 227, and a radio-frequency (RF) amplifier 228. The power supply 227 may be a high voltage, DC power supply connected to an AC source (e.g., line voltage) and provides high voltage, DC power to the RF amplifier 228 via leads 227a and 227b, which then converts high voltage, DC power into treatment energy (e.g., electrosurgical or microwave) and delivers the energy to the active terminal 230. The energy is returned thereto via the return terminal 232. The active and return terminals 230 and 232 and coupled to the RF amplifier 228 through an isolation transformer 229. The RF amplifier 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or RF amplifier 228 allowing the processor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or RF amplifier 228, which adjusts the DC and/or power supply, respectively. Those skilled in the art will appreciate that the processor 225 may be substituted for by using any logic processor (e.g., control circuit) adapted to perform the calculations and/or set of instructions described herein including, but not limited to, field programmable gate array, digital signal processor, and combinations thereof.

The generator 200 according to the present disclosure includes a plurality of sensors 280, e.g., an RF current sensor 280a, and an RF voltage sensor 280b. Various components of the generator 200, namely, the RF amplifier 228, the RF current and voltage sensors 280a and 280b, may be disposed on a printed circuit board (PCB). The RF current sensor 280a is coupled to the active terminal 230 and provides measurements of the RF current supplied by the RF amplifier 228. The RF voltage sensor 280b is coupled to the active and return terminals 230 and 232 provides measurements of the RF voltage supplied by the RF amplifier 228. In embodiments, the RF current and voltage sensors 280a and 280b may be coupled to active and return leads 228a and 228b, which interconnect the active and return terminals 230 and 232 to the RF amplifier 228, respectively.

The RF current and voltage sensors 280a and 280b provide the sensed RF voltage and current signals, respectively, to the controller 224, which then may adjust output of the power supply 227 and/or the RF amplifier 228 in response to the sensed RF voltage and current signals. The controller 224 also receives input signals from the input controls of the generator 200, the instrument 20 and/or forceps 30. The controller 224 utilizes the input signals to adjust power outputted by the generator 200 and/or performs other control functions thereon.

Figure 4:
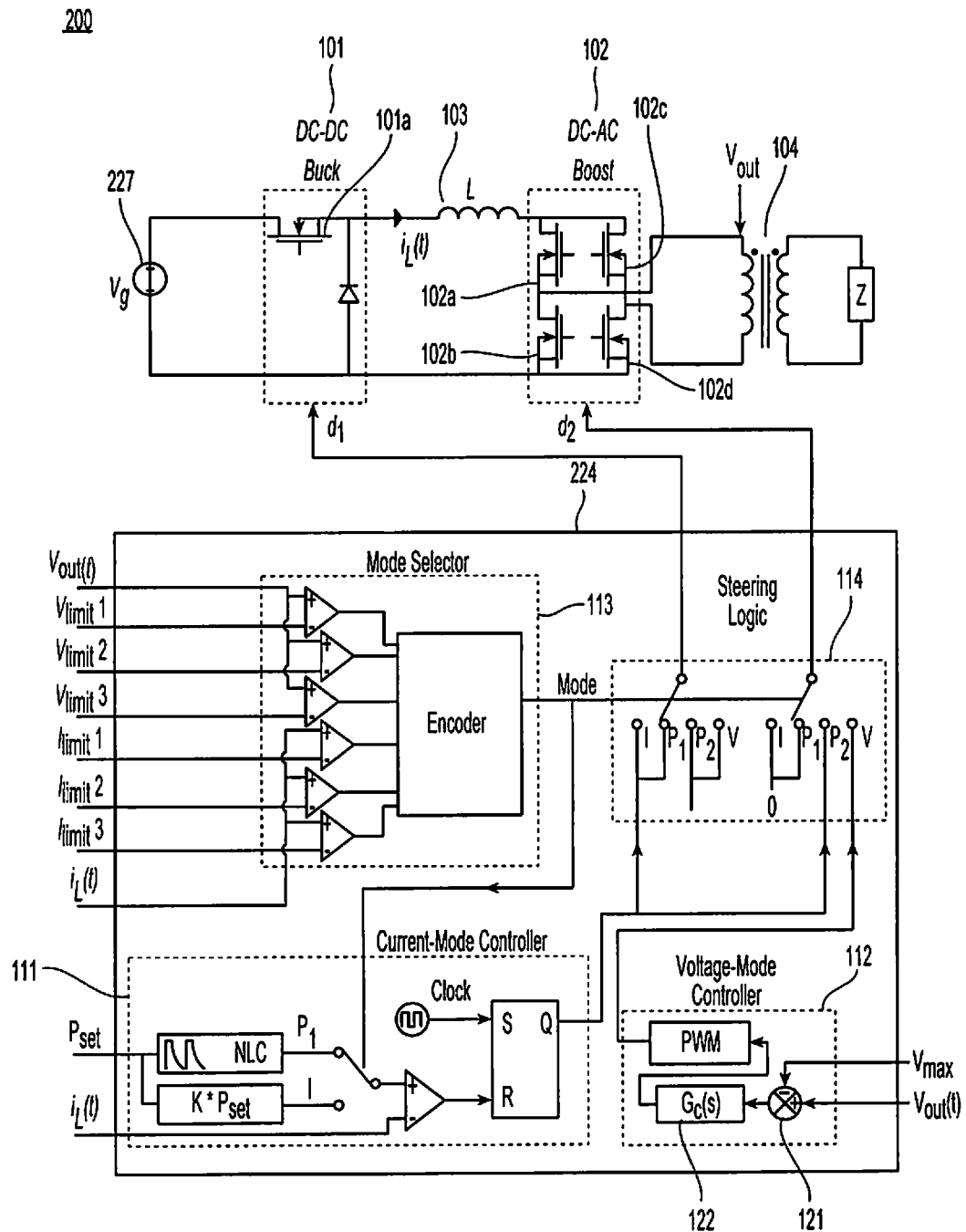
FIG. 4 is a schematic, block diagram of a DC-DC converter and a DC-AC inverter of the electrosurgical generator of FIG. 2 according to the present disclosure.

FIG. 4 shows another embodiment of the generator 200 configured to operate with near-deadbeat control to maintain a desired AC output of generator 200. As used herein, the terms "deadbeat" or "near-deadbeat" refer to adjustments being made by the generator 200 to the output from about 1 cycle of the waveform to about 100 cycles, in embodiments from about 10 cycles to about 25 cycles. The term cycle refers to a full cycle of a waveform (e.g., excitation waveform for igniting ionizable media) having a positive and negative half cycle. The generator 200 according to the present disclosure may have an operating frequency of from about 100 kHz to about 4,000 kHz, and in embodiments, from about 200 kHz to about 3,000 kHz, in further embodiments the frequency may range from about 300 kHz to about 1 MHz, thus, the generator 200 operating at the predetermined frequency of 100 kHz outputs a waveform having 100,000 cycles per second.

The adjustments to the output can be made at the same frequency (e.g., 1 cycle of the electrosurgical waveform) or a factor of about 0.1 (e.g., every 10 cycles of the electrosurgical waveform). In accordance with an exemplary embodiment, near-deadbeat control ensures that only a desired quantum of power is delivered to the electrosurgical instrument. In the prior art generators, slow transient response of the converter to changes in load impedance may result in excessive delivery of power that may not be detected for 500 cycles or more.

The generator 200 is also configured to operate in any of a constant voltage limit mode, a constant current limit mode, a constant power mode, and combinations thereof. The mode selection is generally based on the impedance associated with the load, e.g., gas flow.

With respect to the AC output of the generator 200 and in exemplary embodiments, "constant power" is defined to mean the average power delivered in each switching cycle is substantially constant. Likewise, "constant voltage" and "constant current" are defined as modes where the root mean square (RMS) value of the AC voltage or current, respectively, is regulated to a substantially fixed value.

With reference to the schematic shown in FIG. 4, the generator 200 includes a DC-DC buck converter 101, a DC-AC boost converter 102, an inductor 103, a transformer 104, and the controller 224. In embodiments, the DC-DC buck converter 101 and the DC-AC boost converter 102 are part of the RF output stage 228. In the exemplary embodiment, a DC voltage source Vg, such as the power supply 227, is connected to DC-DC buck converter 101. Furthermore, inductor 103 is electrically coupled between DC-DC buck converter 101 and DC-AC boost converter 102. The output of DC-AC boost converter 102 transmits power to the primary winding of transformer 104, which passes through the secondary winding of transformer 104 to the load Z (e.g., ionizable media).

The DC-DC buck converter 101 includes a switching element 101a and the DC-AC boost converter 102 includes a plurality of switching elements 102a-102d arranged in an H-bridge topology. In embodiments, the DC-AC boost converter 102 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In an exemplary embodiment, controller 224 is in communication with both DC-DC buck converter 101 and DC-AC boost converter 102, in particular, the switching elements 101a and 102a-102d, respectively. The controller 224 is configured to output control signals, which may be a pulse-width modulated signal, to the switching elements 101a and 102a-102d as described in further detail below with respect to the voltage-mode controller 112. The controller 224 is configured to control the duty cycle d1 of the control signal supplied to the switching element 101a of the DC-DC buck converter 101 and the duty cycle d2 of the control signals supplied to the switching elements 102a-102d of the DC-AC boost converter 102. Additionally, controller 224 is configured to measure power characteristics of generator 200, and control generator 200 based at least in part on the measured power characteristics. Examples of the measured power characteristics include, but are not limited to, the current through inductor 103 and the voltage at the output of DC-AC boost converter 102. In an exemplary embodiment, controller 224 controls buck converter 101 by generating the duty cycle d1 based on a comparison of the inductor current and a nonlinear carrier control current for every cycle.

In accordance with an exemplary embodiment, controller 224 may include a current-mode controller 111, a voltage-mode controller 112, a mode selector 113, and steering logic 114. The mode selector 113 compares the output voltage $V_{out}(t)$ and the inductor current $i_L(t)$ to set limits in order to determine the desired mode of operation of the generator 200. The operational mode may be of constant (or maximum) current Imax, constant power $P_1$ from DC-DC buck converter 101, constant power $P_2$ from DC-AC boost converter 102, or constant (or maximum) voltage $V_{max}$, or combinations thereof. The output selection of mode selector 113 is communicated to steering logic 114. In an exemplary embodiment, steering logic 114 controls which of at least one of current-mode controller 111 and voltage mode controller 112 are enabled. Furthermore, steering logic 114 selects which conversion stage receives the output of current-mode controller 111 and/or voltage-mode controller 112.

In one exemplary embodiment, steering logic 114 switches between operating either DC-DC buck converter 101 or DC-AC boost converter 102 with current-mode control for constant power, depending on which portion of the desired output characteristics is being produced. The voltage mode controller 112 and/or current mode controller 111 adjust the duty cycles d1 and/or d2 for current mode control. Furthermore, steering logic 114 selects the duty cycle that each of DC-DC buck converter 101 and/or DC-AC boost converter 102 receives.

The current-mode controller 111 compares the inductor current $i_L(t)$ to nonlinear carrier control current $i_C(t)$ (e.g., desired set point current). In an exemplary embodiment, the nonlinear carrier control current $i_C$ is set by the selection of Pset (e.g., desired power set point), which may be done by a user, or provided by a lookup table. In an exemplary embodiment, current-mode controller 111 uses a latch circuit to compare inductor current $i_L(t)$ to either a current limit signal (I) or a power limit signal ($P_1$). The control signal for the latch circuit is the mode signal, which is communicated from steering logic 114. The inputs of the latch circuit are a clock signal and either the current limit signal (I) or a power limit signal ($P_1$). The selection of the current-mode controller 111 output is in response to the current mode of the generator 200. The operating mode of the generator 200 may be communicated by the mode selector 113. In an exemplary embodiment, the switching waveform d(t) is switched "high" at the start of a switching period if the inductor current $i_L(t)$ is lower than nonlinear carrier control current $i_C(t)$. Furthermore, in the exemplary embodiment, the switching waveform d(t) is switched "low" in response to the inductor current $i_L(t)$ exceeding the nonlinear carrier control current $i_C(t)$. In other words, a comparison of the inductor current $i_L(t)$ to nonlinear carrier control current $i_C(t)$ facilitates adjusting pulse duration of duty cycle d1 of the buck converter 101, as previously described.

To generate and control a constant current from generator 200, the average value of inductor current $i_L(t)$ is set to be substantially equal to fixed control current limit K*Pset. For small inductor current ripple, in other words $\Delta i_L \ll I_L$, the current-mode controller regulates the inductor current $i_L(t)$ to an approximately constant value, which is substantially equal to the fixed control current limit. In accordance with an exemplary embodiment, the current-mode controller 111 is able to maintain an approximately constant value of inductor current $i_L(t)$ by adjusting the current within from about 1 cycle to about 100 cycles, in embodiments from about 2 to about 20 cycles, in further embodiments, from about 3 to about 10 cycles. This low cycle adjustment provides for near-deadbeat or deadbeat control as described above.

In an exemplary embodiment and with continued reference to FIG. 4, voltage-mode controller 112 of the controller 224 includes a comparator 121, a compensator 122, and a pulse-width modulator (PWM) 123. In an exemplary embodiment, voltage-mode controller 112 compares the output voltage $V_{out}(t)$ with a reference voltage $V_{max}$ at comparator 121. The output of comparator 121 is communicated to compensator 122, which in turn, outputs an error signal that drives PWM 123. In the exemplary embodiment, the output of compensator 122 is passed through PWM 123, which sets the duty cycle d2 of the signal in certain modes.

With respect to constant power output mode, constant AC power output is achieved by setting one or both of duty cycle d1 and duty cycle d2 to desired values. In various embodiments, the converter switches of the steering logic 114 between generating constant power using DC-DC buck converter 101 or DC-AC boost converter 102, depending on the impedance of the load. Moreover, in various embodiments, generator 200 may operate both DC-DC buck converter 101 and/or DC-AC boost converter 102 at the same time, which results in a constant power output having a high voltage and low power.

In steady-state and operating at a first constant power level, inductor current $i_L(t)$ is compared to a nonlinear carrier control current $i_C(t)$ in current-mode controller 111. The pulse duration of the duty cycle d1 of the DC-DC buck converter is varied using the current mode controller 111. The varying pulse duration of the duty cycle controls the inductor current $i_L(t)$, which is responsive to the load in contact with the buck converter. As the impedance of the load varies, the voltage across and the current through the inductor 103 also vary. As previously described, at the beginning of the duty cycle, the active portion of the duty cycle is initiated. In response to the inductor feedback signal exceeding the nonlinear carrier control current, the duty cycle switches to the non-active portion. The duty cycle stays in the non-active portion until the end of the duty cycle, upon which the next duty cycle begins in the active portion. In alternative embodiments, during the comparison of the inductor feedback signal and the nonlinear carrier control current, once the control current exceeds the inductor current, the duty cycle switches to the active portion. In accordance with the exemplary embodiment, generator 200 generates constant power using DC-DC buck converter 101.

In steady-state and operating at a second constant power level, the average voltage of $V_1(t)$ is constant in response to the input voltage Vg being constant, the DC-DC buck converter 101 is also disabled, since there is no voltage across inductor 103. The use of current programmed mode control results in the average current of $i_L(t)$ being regulated to an approximately fixed value with deadbeat or near-deadbeat control. In order to regulate $i_L(t)$, duty cycle d2 is varied by the current mode controller to maintain $i_L(t)$ at a fixed value. Given the fixed voltage and current, the power at input of DC-AC boost converter 102 is also constant. In an exemplary embodiment, the DC-AC boost converter 102 is nearly lossless, resulting in the output power being approximately equal to the input power. Since the input power is constant, the output power of DC-AC boost converter 102 is also constant.

With respect to constant voltage output mode, constant voltage output is achieved by setting duty cycle d1 of DC-DC buck converter 101 to a fixed value, and duty cycle d2 of DC-AC boost converter 102 is voltage-mode controlled. In an exemplary embodiment, the voltage-mode control involves measuring the output voltage of DC-AC boost converter 102 with a sensor network, feeding the sensed output voltage to a control loop in voltage-mode controller 112, and adjusting the converter's duty cycle command based on the relative difference between the measured output voltage and the reference output voltage. In other words, the duty cycle d2 is set to increase or decrease the output voltage to match $V_{limit}$. In an exemplary embodiment, $V_{limit}$ may be set by a user or based on values in a look-up table. In an alternative embodiment, the boost inverter is run at a fixed duty cycle with no feedback of the output voltage.

With respect to constant current output mode, constant current output is achieved by operating DC-AC boost converter 102 at a fixed duty cycle d2 and current-mode controlling DC-DC buck converter 101. In an exemplary embodiment, the current-mode control accurately controls the average inductor current such that the output of buck converter 101 is a constant current. In one constant current embodiment, current-mode controller 111 compares inductor current $i_L(t)$ to a constant current $i_c$, which is set by K*Pset, where K*Pset is a constant current set by the user during use. In various embodiments, Pset is set during the design stage.

In other words, controller 224 is configured to vary duty cycle d1 in order to maintain inductor current $i_L(t)$ at the fixed value. As a result, the constant current output mode produces an AC output current whose magnitude is regulated with near-deadbeat speed. In an exemplary embodiment, the generator 200 implementing the three modes of constant power, constant voltage, or constant current produces a very fast, very accurate regulation of the AC output characteristic. Various modes are impacted by monitored characteristics, while other modes do not need to respond to the same monitored characteristics. Specifically, controller 224 may switch between operating modes based in part on monitored characteristics, such as inductor current and voltage. In other words, the selection of which stage of the converter to current-mode control is achieved with minimal feedback and without a need for extraneous measurements, averaging, or feedback of the output. Also, and as previously mentioned, the controller 224 performs near deadbeat control by regulating inductor current to an approximately constant value, equal to a reference current.

Transitioning between the three modes, in an exemplary embodiment, is determined by monitoring the voltage of the primary winding of transformer 104 and the inductor current. Furthermore, the determination of transitioning between the modes is also based on the voltage and current of inductor 103. The controller 224 transitions modes from constant current to constant power to constant voltage as the output voltage increases. Specifically, in an exemplary embodiment, the generator 200 operates in the constant current mode if the output voltage is less than a first voltage limit ($V_{limit\_1}$). If the output voltage exceeds the first voltage limit, the generator 200 transitions to a first constant power mode (P1). If the output voltage exceeds a second voltage limit ($V_{limit\_2}$), the generator 200 transitions to a second constant power mode (P2). If the output voltage exceeds a third voltage limit ($V_{limit\_3}$), the generator 200 transitions to the constant voltage mode, where the output voltage is limited and held constant. In an exemplary embodiment, the first voltage limit ($V_{limit\_1}$), the second voltage limit ($V_{limit\_2}$), and the third voltage limit ($V_{limit\_3}$) are set by a user or by the generator 200 (e.g., from a look-up table).

Similarly, an exemplary controller 224 transitions from constant voltage mode to constant power mode and to constant current mode as inductor current $i_L(t)$ increases. Specifically, in an exemplary embodiment, the generator 200 operates in the constant voltage mode if the inductor current does not exceed a first current limit ($I_{limit\_1}$). If the inductor current does exceed the first current limit ($I_{limit\_1}$), then the mode transitions to the second constant power level. If the inductor current exceeds a second current limit ($I_{limit\_2}$), then the mode transitions to the first constant power level. If the inductor current exceeds a third current limit ($I_{limit\_3}$), the generator 200 transitions to the constant current mode, where the inductor current is limited and held constant. In an exemplary embodiment, the first current limit ($I_{limit\_1}$), the second current limit ($I_{limit\_2}$), and the third current limit ($I_{limit\_3}$) are set by a user or by the generator (e.g., from a look-up table).

As described above, in order to achieve the constant current, the DC-DC buck converter 101 is controlled in current-program mode (CPM) and the DC-AC boost converter 102 is fixed at about 100% duty cycle d2. In order to achieve constant power, in one embodiment the DC-DC buck converter 101 may be controlled in non-linear carrier control (NLC) mode and the DC-AC boost converter 102 is fixed at about 100% duty cycle d2. In another embodiment, the DC-DC buck converter 101 is fixed at about 100% duty cycle d1 and the DC-AC boost converter 102 is controlled in CPM. In order to achieve constant voltage, the DC-DC buck converter 101 may be fixed at 100% duty cycle d1 and the DC-AC boost converter 102 is fixed at a predetermined duty cycle d2, which may be less than 100%.

The generator 200 according to the present disclosure is capable of outputting energy for generating plasma having any user-settable frequency, such that the waveforms have an infinitely variable frequency, which may be adjusted without terminating energy generation. In embodiments, the frequency may be adjusted manually, e.g., by the user, or automatically, e.g., by the generator 200, in response to energy delivery feedback or any other suitable parameter, e.g., time, as described in further detail below. Adjustments to the frequency may be accomplished at the DC-AC boost converter 102. In particular, the controller 224 adjusts the duty cycle d2 of the control signals supplied to the switching elements 102a-102d of the DC-AC boost converter 102.

In embodiments, the generator 200 may include discrete frequency settings, which may be input via the user interface 241 and/or the instrument 12. In further embodiments, the generator 200 may include an input for continuously varying the frequency. The user interface 241 may include a setting to adjust the crest factor. In further embodiments, the instrument 12 or other input devices (e.g., foot switch) may include inputs to adjust the frequency. In additional embodiments, the frequency may be adjusted by the controller 224 automatically based on changes in energy, plasma, tissue properties (e.g., impedance), ionizable media flow rate, and combinations thereof. In particular, the generator 200 may measure any suitable energy, plasma and/or tissue parameter using the sensors 280 including, but not limited to, voltage, current, phase, impedance, ionizable media flow rate, and combinations thereof and automatically adjust the frequency in response to this measurement.

With reference once again to FIG. 1, the system 10 provides a flow of plasma through the instrument 12 to a workpiece (e.g., tissue). Plasma feedstocks, which include ionizable media and optional precursor feedstocks, are supplied by the ionizable media source 16 to the plasma instrument 12. The ionizable media source 16 may include various flow sensors and controllers (e.g., valves, mass flow controllers, etc.) to control the flow of ionizable media to the instrument 12. The flow rate may be adjusted to provide for laminar flow rate, turbulent flow rate, and any combinations thereof. During operation, the ionizable media and/or the precursor feedstock are provided to the plasma instrument 12 where the plasma feedstocks are ignited to form plasma effluent containing ions, radicals, photons from the specific excited species and metastables that carry internal energy to drive desired chemical reactions in the workpiece or at the surface thereof. The feedstocks may be mixed upstream from the ignition point or midstream thereof (e.g., at the ignition point) of the plasma effluent.

The ionizable media source 16 may include a storage tank, a pump, and/or flow meter (not explicitly shown). The ionizable media may be a liquid or a gas such as argon, helium, neon, krypton, xenon, radon, carbon dioxide, nitrogen, hydrogen, oxygen, etc. and their mixtures, and the like. These and other gases may be initially in a liquid form that is gasified during application. The precursor feedstock may be either in solid, gaseous or liquid form and may be mixed with the ionizable media in any state, such as solid, liquid (e.g., particulates or droplets), gas, and the combination thereof.

With continued reference to FIG. 1, the ionizable media source 16 may be coupled to the plasma instrument 12 via tubing 14. The tubing 14 may be fed from multiple sources of ionizible media and/or precursor feedstocks, which may be combined into unified tubing to deliver a mixture of the ionizable media and the precursor feedstock to the instrument 12 at a proximal end thereof. This allows for the plasma feedstocks, e.g., the precursor feedstock and the ionizable gas, to be delivered to the plasma instrument 12 simultaneously prior to ignition of the mixture therein.

Ionizable media may be measured using a gas flow sensor (not shown) disposed within the instrument 12 or anywhere along the tubing 14 and/or at the ionizable media source 16. The gas flow sensor is coupled to the generator 200 and provides flow rate measurements to the generator 200 for adjustment of the frequency in response to the flow rate measurement. In embodiments, the flow rate of ionizable media may be determined using impedance and other electrical properties at the generator 200 using the sensors 280.

In another embodiment, the ionizable media and precursor feedstocks may be supplied at separate connections, such that the mixing of the feedstocks occurs within the plasma instrument 12 upstream from the ignition point such that the plasma feedstocks are mixed proximally of the ignition point.

In a further embodiment, the plasma feedstocks may be mixed midstream, e.g., at the ignition point or downstream of the plasma effluent, directly into the plasma. It is also envisioned that the ionizable media may be supplied to the instrument 12 proximally of the ignition point, while the precursor feedstocks are mixed therewith at the ignition point. In a further illustrative embodiment, the ionizable media may be ignited in an unmixed state and the precursors may be mixed directly into the ignited plasma. Prior to mixing, the plasma feedstocks may be ignited individually. The plasma feedstock may be supplied at a predetermined pressure to create a flow of the medium through the instrument 12, which aids in the reaction of the plasma feedstocks and produces a plasma effluent. The plasma according to the present disclosure may be generated at or near atmospheric pressure under normal atmospheric conditions.

In one embodiment, the precursors may be any chemical species capable of forming reactive species such as ions, electrons, excited-state (e.g., metastable) species, molecular fragments (e.g., radicals) and the like, when ignited by electrical energy from the generator 200 or when undergoing collisions with particles (electrons, photons, or other energy-bearing species of limited and selective chemical reactivity) formed from ionizable media 16. More specifically, the precursors may include various reactive functional groups, such as acyl halide, alcohol, aldehyde, alkane, alkene, amide, amine, butyl, carboxlic, cyanate, isocyanate, ester, ether, ethyl, halide, haloalkane, hydroxyl, ketone, methyl, nitrate, nitro, nitrile, nitrite, nitroso, peroxide, hydroperoxide, oxygen, hydrogen, nitrogen, and combination thereof. In embodiments, the precursor feedstocks may be water, halogenoalkanes, such as dichloromethane, tricholoromethane, carbon tetrachloride, difluoromethane, trifluoromethane, carbon tetrafluoride, and the like; peroxides, such as hydrogen peroxide, acetone peroxide, benzoyl peroxide, and the like; alcohols, such as methanol, ethanol, isopropanol, ethylene glycol, propylene glycol, alkalines such as sodium hydroxide, potassium hydroxide, amines, alkyls, alkenes, and the like. Such precursor feedstocks may be applied in substantially pure, mixed, or soluble form.

With reference to FIGS. 1, 5, and 6, the instrument 12 includes a handle housing 100 having a proximal end 102 and a distal end 104. The housing 100 also includes a lumen 106 defined therein having a proximal end coupled to the gas tubing 14 from the ionizable media source 16 and a distal end terminating at the distal end 104 of the housing 100. The instrument 12 also includes an elongated body 120 having a shaft housing 122 defining a lumen 124 therethrough as shown in FIG. 6. The shaft housing 122 may be rigid or flexible. In particular, the lumens 106 and 124 are in gaseous and/or fluid communication with the ionizable media source 16 allowing for the flow of ionizable media and precursor feedstocks to flow through the lumens 106 and 124.

With reference to FIGS. 5 and 6, conductors 4a, 4b are coupled to the electrodes 108 and 110 (FIG. 6), respectively. The conductors 4a, 4b extend through the housing 100 and shaft housing 122 of the elongated body 120 and are connected to the generator 200 via the cable 4. The cable 4 may include a plug (not shown) connecting the instrument 12 to the generator 200 at the connector 258. The conductor 4a is coupled to the proximal end of the electrode 108. The conductor 4b may be a lead or a wire embedded in the shaft housing 122 and is coupled to the electrode 110 by exposing a distal portion of the conductor 4b.

The shaft housing 122 may have a diameter from about 2 mm to about 20 mm allowing the instrument 12 to be inserted through operating ports of an endoscope or access ports in laparoscopic procedures as well as natural body orifices for application of the plasma effluent at the operating site during minimally invasive procedures.

The shaft housing 122 may be formed from any suitable dielectric material including thermoplastics, such as acrylics, celluloid, cellulose acetate, cyclic olefin copolymer, ethylene-vinyl acetate, fluoropolymers (e.g., polytetrafluoroethylene), ionomers, polyoxymethylene, polyacrylates, polyacrylonitrile, polyamide, polyamide-imide, polyaryletherketon, polybutadiene, polybutylene, polybutylene terephthalate, polycaprolactone, polychlorotrifluoroethylene, polyethylene terephthalate, polycyclohexylene dimethylene terephthalate, polycarbonate, polyhydroxyalkanoates, polyketones, polyester, polyethylene, polyetheretherketone, polyetherketoneketone, polyetherimide, polyethersulfone, chlorinated polyethylene, polyimide, polylactic acid, polymethylpentene, polyphenylene oxide, polyphenylene sulfide, polyphthalamide, polypropylene, polystyrene, polysulfone, polytrimethylene terephthalate, polyurethane, polyvinyl acetate, polyvinyl chloride, polyvinylidene chloride, styrene-acrylonitrile, and combinations thereof.

With reference to FIG. 6, the instrument 12 further includes an applicator tip 130 coupled to the elongated body 120 at the distal end thereof. In embodiments, the applicator tip 130 is inserted into the distal end of the lumen 124. The tip 130 may be formed from any suitable dielectric materials including the thermoplastic materials described above if the temperature of the plasma is sufficiently low or any other suitable heat-resistant dielectric material, including ceramic materials. Suitable ceramic materials include, but are not limited to, metal oxide ceramics, non-oxide ceramics, ceramic composites, and combinations thereof. Suitable oxide ceramics include zirconium oxide, aluminum oxide, silica oxide, magnesium oxide, iron oxide, calcium oxide, yttrinum oxide, cerium oxide, alumina oxide, silicon oxide, calcium silicate, copper oxide, nickel oxide, praseodymium oxide, titanium oxide, erbium oxide, europium oxide, holmium oxide, chromium oxide, manganese oxide, vanadium oxide, cobalt oxide, neodymium oxide and combinations and composites thereof such as fiber composites, metal oxide composites, non-oxide composites, alumina/zirconia composites, and the like.

The applicator tip 130 also includes a lumen 136 defined therethrough that is fluid communication with the lumen 124. The lumen 136 may have any suitable shape for tailoring the size and/or shape of the plasma plume generated by the instrument 12. In embodiments, the lumen 124 may also include one or more surfaces for further shaping (e.g., narrowing) the plasma plume prior to exiting the instrument 12.

With reference to FIG. 6, the instrument 12 also includes two or more electrodes 108, 110 disposed within the applicator tip 130, shown as inner and outer electrodes, respectively. The electrodes 108 and 110 may be formed from a conductive material including metals, such as stainless steel, copper, aluminium, tungsten, and combinations and alloys thereof. The electrodes 108 and 110 may have any suitable shape for conducting electrical energy and igniting the ionizable media including, but not limited to, rings, strips, needles, meshes, and the like. The electrodes 108 and 110 may also be disposed outside or within the lumen 124 for capacitive coupling with the ionizable media as described in further detail below. The ionizable media in conjunction with the optional precursor feedstocks is ignited by application of energy through the electrodes 108 and 110 to form a plasma plume exiting through an opening 115 of the applicator tip 130.

In embodiments, the electrode 108 may be configured as an inner electrode as shown in FIG. 6. The electrode 108 may be enclosed in an insulative layer 108a and may be supported within the lumen using a spacer 113. The electrode 110 is disposed on an outer surface 132 of the applicator tip 130. The electrode 110 may include one or more electrodes that are insulated from the electrode 108 by the dielectric material of the applicator tip 130 allowing for capacitive coupling between the electrodes 108 and 110.

In further embodiments, the instrument 12 may include an identifier (not shown) that is configured to store one or more values corresponding to properties of the instrument 12. The identifier may be RFID, EEPROM or any other suitable storage medium accessible by the generator 200. Values stored in the identifier may include, but are not limited to, electrode type/structure, dimensions of the applicator tip 130, shape/structure of the lumen 136, serial number, and the like. In further embodiments, the storage medium (e.g., non-transitory) identifier may be wholly or partially rewritable and may store usage data including sterilization counts, usage counts, time used and the like. The generator 200 may include a corresponding reader/writer configured to interface with the identifier 119. The generator 200 may tailor its output based on the data stored in the identifier as well as update the identifier to reflect usage/sterilization data after the instrument 12 is used.

With reference to FIGS. 1 and 5, the instrument 12 also includes one or more activation switches 150a, 150b, 150c, each of which extends through top-half shell portion of housing 100. Each activation switch 150a, 150b, 150c is operatively supported on a respective tactile element (e.g., a snap-dome switch) provided on a switch plate 154. Each activation switch 150a, 150b, 150c controls the transmission of electrical energy supplied from generator 200 to the electrodes 108 and 110. The activation switches 150a-150c transmit control signals via a voltage divider network (VDN) or other circuit control means through control leads within the cable 4 to the generator 200. For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series, which are provided with taps at certain points to make available a fixed or variable fraction of the applied voltage.

With reference back to FIG. 1, the instrument 12 further includes a variable setting element, e.g., slide switch 158 slidingly supported on or within housing 100 in a guide channel 160 defined therein. The switch 158 may be configured to function as a slide potentiometer, sliding over and along VDN. The switch 158 has a first position at a proximal-most position (e.g., closest to cable 4) corresponding to a lowest frequency setting, a second position wherein the switch 158 is at a distal-most position corresponding to highest frequency setting. The switch 158 may be disposed in a plurality of intermediate positions wherein the switch 158 is at positions between the distal-most position and the proximal-most position corresponding to various intermediate frequency settings. As can be appreciated, the frequency settings from the proximal end to the distal end may be reversed, e.g., high to low. Activation switches 150a-150c and the switch 158 are described in further detail in a commonly-owned U.S. Pat. No. 7,879,033, the entire contents of which are incorporated by reference herein.

Frequency may be controlled either through the generator 200 and/or the instrument 12. With reference to FIG. 2, the screen 244 may be a touchscreen that allows for control of the outputs the connectors 256 and 258 as well as the frequency of the generator 200. In embodiments, the screen 244 may be replaced and/or supplemented by other controls (e.g., keyboard, buttons, etc.). The screen 244 includes input buttons for adjusting the frequency. This may be accomplished by a variety of control schemes, shown on the screen 244 as graphical user interface elements, such as a variable setting element (e.g., slidable bar), predefined increment buttons, text and/or number inputs, and combinations thereof. The frequency settings may be displayed as a slider of suitable frequency settings, discrete frequency input, numerical input, or any other input for setting frequency. The frequency settings are used by the generator 200 to adjust the frequency as described above to achieve a desired frequency of the excitation energy for the plasma outputted by the instrument 12.

The instrument 12 may also control various properties of the plasma beam. The activation switches 150a-150c may be used to activate the generator 200 and/or to control the flow of ionizable media from the ionizable media source 16. The slide switch 158 is configured to adjust the frequency as described above to achieve a desired degree of frequency of the plasma outputted by the instrument 12.

In embodiments, additional input devices may be used such as foot switches or handheld keyboards and/or remotes. The input devices (e.g., activation switches 150a-150c) may be two-stage switches where upon activation of the first stage, ionizable media and RF energy are supplied to the instrument 12 at a sufficient level to prime the active plasma field within the lumen 106 to initiate non-therapeutic ionization. This enables the user to visualize the target tissue relative to the non-therapeutic ionized gas plume. The generator 200 may include a feedback control loop to ensure the pre-ionization level is achieved and maintained at minimum needed RF power. In embodiments, a single wave spike may be generated to maintain sufficient ionized field without over heating the plasma instrument by minimizing RMS power delivered to pre-ionization field. In further embodiments, trace amounts of substantially non-electronegative compositions may be added to improve visibility of the ionized gas. Suitable tracer compositions include compounds such as sodium, neon, xenon, combinations thereof, and the like. The closure of the second stage of the switch increases RF power to therapeutic levels thereby initiating targeted therapeutic results.

The present disclosure provides for a plasma electrosurgical system with variable frequency, which allows for real-time adjustment of the plasma beam, thereby allowing for achieving specific surgical effects. The system allows for a single electrosurgical generator to be used for generating various plasma effects thereby reducing the cost of operating room equipment. In particular, combination of low and high-temperature plasma in a single instrument improves the utility of both technologies, and may permit novel surgical techniques, such as surface sterilization of tissue using cold plasma followed by dissection using hot plasma, or dissection using hot plasma followed by cold plasma drug delivery.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. In particular, as discussed above this allows for tailoring of the relative populations of plasma species to meet needs for the specific process desired on the workpiece surface or in the volume of the reactive plasma.

What is claimed is:

1. A plasma system comprising:
   a plasma instrument;
   an ionizable media source in fluid communication with the plasma instrument and configured to supply ionizable media thereto; and
   a variable frequency energy source coupled to the plasma instrument and configured to:
      supply an excitation waveform including a plurality of cycles to the plasma instrument sufficient to ignite the ionizable media supplied by the ionizable media source to generate a plasma effluent; and
      adjust a frequency of the excitation waveform on a cycle-by-cycle basis to a first frequency at which the plasma effluent is at a first temperature for non-thermal treatment of tissue and a second frequency, higher than the first frequency, at which the plasma effluent is at a second temperature, higher than the first temperature, for thermal treatment of tissue.

2. The plasma system according to claim 1, wherein the ionizable media source is adapted to be coupled to the variable frequency energy source.

3. The plasma system according to claim 2, wherein the variable frequency energy source is configured to adjust the frequency based on a flow rate of the ionizable media from the ionizable media source.

4. The plasma system according to claim 1, wherein the plasma instrument includes:
   an elongated body defining a lumen therethrough;
   a first electrode and a second electrode; and
   a slide switch for varying a frequency of supplied energy.

5. The plasma system according to claim 4, wherein the plasma instrument includes an applicator tip coupled to a distal end of the elongated body.

6. The plasma system according to claim 5, wherein the applicator tip defines a second lumen in fluid communication with the lumen of the elongated body.

7. The plasma system according to claim 6, wherein the first electrode is disposed on an outer surface of the applicator tip.

8. The plasma system according to claim 7, wherein the second electrode is disposed within at least one of the lumen of the elongated body or the second lumen.

9. The plasma system according to claim 1, wherein the variable frequency energy source includes:
   a non-resonant radio frequency output stage configured to output the excitation waveform; and
   a controller coupled to the non-resonant radio frequency output stage, the controller configured to adjust the frequency of the excitation waveform on a cycle-by-cycle basis.

10. The plasma system according to claim 9, wherein the non-resonant radio frequency output stage includes:
    a DC-DC buck converter configured to output a DC waveform, the DC-DC buck converter including at least one first switching element operated at a first duty cycle.

11. The plasma system according to claim 10, wherein the non-resonant radio frequency output stage further includes:
    a DC-AC boost converter coupled to the DC-DC buck converter and including at least one second switching element operated at a second duty cycle, the DC-AC boost converter configured to convert the DC waveform to generate the excitation waveform.

12. The plasma system according to claim 11, wherein the controller is coupled to the DC-DC buck converter and the DC-AC boost converter and the controller is further configured to adjust the second duty cycle of the excitation waveform.

13. A method comprising:
    supplying ionizable media from an ionizable media source to a plasma instrument;
    supplying an excitation waveform including a plurality of cycles from a variable frequency energy source to the plasma instrument to ignite the ionizable media supplied by the ionizable media source and to generate a plasma effluent at a first frequency at which the plasma effluent is at a first temperature for non-thermal treatment of tissue or at a second frequency higher than the first frequency at which the plasma effluent is at a second temperature higher than the first temperature for thermal treatment of tissue; and
    adjusting a frequency of the excitation waveform between the first frequency of the excitation waveform and the second frequency of the excitation waveform on a cycle-by-cycle basis.

14. The method according to claim 13, wherein adjusting of the frequency includes inputting a desired frequency using a frequency user interface of the variable frequency energy source.

15. The method according to claim 13, wherein adjusting of the frequency includes inputting the frequency based on a flow rate of the ionizable media from the ionizable media source.

16. The method according to claim 13, wherein supplying the excitation waveform includes operating at least one switching element of a DC-AC boost converter at a duty cycle to convert a DC waveform to generate the excitation waveform.

17. The method according to claim 16, wherein adjusting of the frequency includes adjusting the duty cycle.

* * * * *